United States Patent
Liu et al.

(10) Patent No.: US 7,924,008 B2
(45) Date of Patent: Apr. 12, 2011

(54) VIBRATIONALLY DECOUPLED PATIENT TABLE FOR USE IN MAGNETIC RESONANCE SYSTEM

(75) Inventors: Ke Cheng Liu, Zhejiang Hangzhou (CN); Xiao Guang Liu, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/321,908

(22) Filed: Jan. 27, 2009

(65) Prior Publication Data

US 2009/0189608 A1 Jul. 30, 2009

(30) Foreign Application Priority Data

Jan. 29, 2008 (CN) .................... 2008 2 0001565 U

(51) Int. Cl.
*G01V 3/00* (2006.01)
(52) U.S. Cl. ........................... 324/318; 324/321
(58) Field of Classification Search .......... 324/300–322; 600/410, 411, 421, 422
See application file for complete search history.

(56) References Cited

U.S. PATENT DOCUMENTS

| | | | |
|---|---|---|---|
| 6,794,871 B2 * | 9/2004 | Imai et al. ...................... | 324/318 |
| 7,218,106 B2 * | 5/2007 | Yasuhara et al. ............... | 324/307 |
| 7,567,082 B2 * | 7/2009 | Takamori ...................... | 324/318 |
| 2003/0062898 A1 * | 4/2003 | Imai et al. ...................... | 324/318 |
| 2005/0122108 A1 * | 6/2005 | Yasuhara et al. ............... | 324/318 |
| 2007/0164743 A1 * | 7/2007 | Takamori ...................... | 324/318 |
| 2007/0238963 A1 * | 10/2007 | Kaminaga et al. ............ | 600/407 |
| 2008/0246478 A1 * | 10/2008 | Kato .............................. | 324/318 |
| 2009/0189608 A1 * | 7/2009 | Liu et al. ....................... | 324/321 |
| 2010/0219347 A1 * | 9/2010 | Schulz et al. ............ | 250/363.04 |

* cited by examiner

*Primary Examiner* — Melissa J Koval
*Assistant Examiner* — Tiffany A Fetzner

(57) ABSTRACT

The present utility model discloses a patient table for a magnetic resonance system, said magnetic resonance system also comprises a body coil, and said patient table comprises a table board and supporting means for supporting said table board, which table board is located in said body coil, and said supporting means supports said table board in such a way that the table board has no contact with said body coil. By using said patient table according to the present utility model, it is possible to eliminate the vibration of the table board caused by the vibration of a gradient coil, thus improving the imaging quality.

15 Claims, 2 Drawing Sheets

VIBRATIONALLY DECOUPLED PATIENT TABLE FOR USE IN MAGNETIC RESONANCE SYSTEM

CROSS REFERENCE TO RELATED APPLICATIONS

This application claims priority of Chinese application No. 200820001565.1 filed Jan. 29, 2008, which is incorporated by reference herein in its entirety.

FIELD OF THE INVENTION

The present utility model relates to the magnetic resonance technology and, particularly, to a patient table used in a magnetic resonance system.

BACKGROUND OF THE INVENTION

Currently, among the models of implementation of patient tables (PTAB) for magnetic resonance systems, particularly for cylindrical magnetic resonance systems, a table board in such a patient table is supported by a body coil (BC) in the magnetic resonance system. The patient table mentioned here comprises various construction components, such as a supporting frame, a table board, a driving mechanism and so on. In which, the body coil is generally a radio frequency body coil fixed on the inner diameter of the magnet. At the same time, gradient coils, including all the gradient coils and shimming coils, are also fixed directly onto the inner diameter of the magnet.

FIG. 1 and FIG. 2 are respective schematic views of two types of patient tables of different models of implementation currently available on the market for use in magnetic resonance systems. As shown in FIG. 1, a gradient coil 102 is fixed directly onto a magnet 101; at the same time, a body coil 103 is also fixed on the magnet 101 via body coil tubes 104 which are in horizontal and vertical directions as shown in FIG. 1. In practical applications, the body coil 103 and its tubes 104 are exhibited as a circular hole, wherein the position of the vertical tube (the tube in the vertical direction shown in FIG. 1) is approximately located at a position that when the circular hole is equally divided into three angles, the position corresponds to the position of two edges of the lower angle of the circular hole; a support frame 105 is fixed at one side of the magnet 101, for example, the right side as shown in FIG. 1; a driving mechanism 106 located on the supporting frame 105 drives a table board 107 to move in the horizontal direction; when it is located outside the magnet 101, the table board 107 is moved on a travel rail (not shown) of the patient table itself, the table board 107, when entering into the magnet 101, is supported by the travel rail of the body coil 103, for example, on a relatively flat region above the body coil 103. The implementation model shown in FIG. 2 is similar to that in FIG. 1, which also comprises construction components such as a magnet 201, a gradient coil 202, a body coil 203, body coil tubes 204, and so on, and what differs from the implementation model shown in FIG. 1 lies only in that a supporting frame 205 in the patient table has no contact with the magnet 201, it is mounted directly on the ground, however, when a table board 207 enters into the magnet 201 under the driving of a driving mechanism 206, the table board 207 is likewise supported by the rail of the body coil 203.

It can be seen that, in both of these two implementation models of the current patient table, they rely on the rail of the body coil to support the table board, thus, in practical applications, they lead to the following problems:

During a scanning process with a magnetic resonance system, the intense current in a gradient coil will cause the gradient coil to vibrate. The reason is that the gradient coil is distorted under the effect of Lorentz force. The distortion is a function of the coil current and is determined by the waveform required by the scanning.

Since the body coil and the gradient coil are both fixed on the magnet, the vibration of the gradient coil will be transmitted to the body coil during the scanning process; therefore, the vibration of the body coil will be transmitted to the table board. This situation generally occurs in the case that the gradient coil operates under an intense load, i.e., the current is continuously large and the intervals between gradient pulses are very short, while the load of the table board is very light, so mechanical resonance vibration occurs. At this time, the vibration frequency of the gradient coil usually covers the natural frequency of the table board, thus it causes the table board to vibrate, and in turn it causes the scanned object carried on the table board, e.g. a human body, to vibrate, particularly when the weight of the object is relatively small, i.e., the load of the table board is relatively small. This situation occurs particularly easily in applications of the pediatric departments, when an infant (with a weight of 2 Kg-20 Kg) is scanned at the scanning position for an adult's brain.

Such vibration would not cause any problem ten years ago and even now in a low field system which only requires a relatively lower image resolution (sizes of pixels are greater than or equal to 2-3 mm). However, with the improvements in the performance of magnetic resonance systems, especially with the ever increasing field intensity and gradient performance, magnetic resonance images of high resolution at a sub-millimeter order have become possible. Under such circumstances, any tiny vibration of amplitude of a sub-millimeter order, for example, the vibration with an amplitude of 0.1 millimeter, will produce serious effects on the image quality, leading to the blurring of image pixels.

Moreover, it has been discovered recently that, the images obtained by high resolution diffusion tensor imaging (DTI) are affected by the serious absence of signals, which may be due to the dephasing caused by vibration. For example, the mechanical vibration caused by the high intensity gradient pulses in the horizontal direction will cause a severe phenomenon of absence of signals. The phenomenon of absent signals actually appears as there is a region at a certain position, for example, a middle position, in an image obtained by scanning which is referred to as a black hole of signals, and DTI analysis cannot be performed on the basis of such image quality; while for the same object and slice position, when more load such as 30 Kg is loaded on the table board, or when the load distribution is adjusted, the phenomenon of absent image signals will be improved significantly due to the reduced vibration.

In summary, in currently available patient tables, since they rely on the rail of the body coil to support the table board, and there also exist mechanical resonances between the body coil and the magnet, the vibration of the gradient coil during scanning will be transmitted from the magnet to the body coil, and eventually causes the vibration of the loaded object on the table board, thus leading to a reduced image quality.

SUMMARY OF THE INVENTION

A main object of the present utility model is to provide a patient table for use in a magnetic resonance system, which is capable of eliminating the vibration of the table board caused by the vibration of a gradient coil, thus improving the imaging quality.

In order to achieve the abovementioned object, the technical solution of the present utility model is implemented as follows:

a patient table for use in a magnetic resonance system, wherein said magnetic resonance system also comprises a body coil, and said patient table comprises a table board and supporting means for supporting said table board, and during scanning, said table board is located in said body coil, and said supporting means support said table board in such a way that the table board has no contact with said body coil.

In which case, said magnetic resonance system further comprises a magnet; said supporting means comprise a first supporting frame, a second supporting frame, a driving mechanism and a travel rail;

said first supporting frame and said second supporting frame are located at two sides of said magnet respectively without contacting said magnet, and support two ends of said travel rail respectively, so as to support said travel rail and said body coil in such a way as to have a certain gap there between; and said driving mechanism drives said table board to move on said travel rail during scanning.

Said driving mechanism is located between said first supporting frame and said travel rail.

Alternatively, said magnetic resonance system further comprises a magnet; said supporting means comprise a first supporting frame, a second supporting frame, a first driving mechanism, a second driving mechanism and a supporting member; said first supporting frame and said second supporting frame are located at two sides of said magnet respectively without contacting said magnet; and said supporting member and said second supporting frame are located at the same side;

said first driving mechanism is used for driving said table board to move in a horizontal direction to an imaging position, and for driving said first supporting frame up when said supporting member enters into one end at the bottom of said table board, so as to lift the other end of said table board to a predetermined height, and to keep a certain gap with said body coil; and said second driving mechanism is used for driving said supporting member to enter into said one end at the bottom of the table board when said table board is moved to the imaging position, and for driving said second supporting frame to lift so as to lift said supporting member and the table board thereon to a predetermined height, and to keep a certain gap with said body coil.

The predetermined heights to which the two ends of said table board are lifted are the same.

Said first driving mechanism is further used for driving said first supporting frame up or down when said table board is moved out of the magnet.

Said first driving mechanism is located between said first supporting frame and said table board; said second driving mechanism is located between said second supporting frame and said supporting member; and said supporting member is fixed onto said second driving mechanism.

Said first supporting frame and said second supporting frame are fixed on the ground.

It can be seen that, by using a patient table according to the present utility model, and by the design of the table board, the table board is made to have no contact with the body coil during scanning, so that the vibration of the table board caused by the vibration of the gradient coil is eliminated, and the imaging quality during scanning is improved.

BRIEF DESCRIPTION OF THE DRAWINGS

The above and other features and advantages of the present utility model will be become more apparent to those skilled in the art by the detailed description of the preferred embodiments of the present utility model below with reference to the accompanying drawings, wherein.

DETAILED DESCRIPTION OF THE INVENTION

The present utility model will be further described in detail below in conjunction with accompanying drawings and embodiments to make the purpose, technical solutions and advantages of the present utility model clearer and more apparent. It should be understood that the embodiments described here are merely for illustrating the present utility model and are not intended to limit the present utility model.

In order to solve the problems existing in the prior art, in the embodiments of the present utility model a patient table for use in a magnetic resonance system is proposed, in which an independent floating method is adopted: during the process of scanning, a table board and a gradient coil are fixed onto different objects. Said patient table comprises a table board and supporting means for supporting the table board, and during scanning the supporting means support the table board to pass through a body coil without contacting the body coil.

Figure 1:
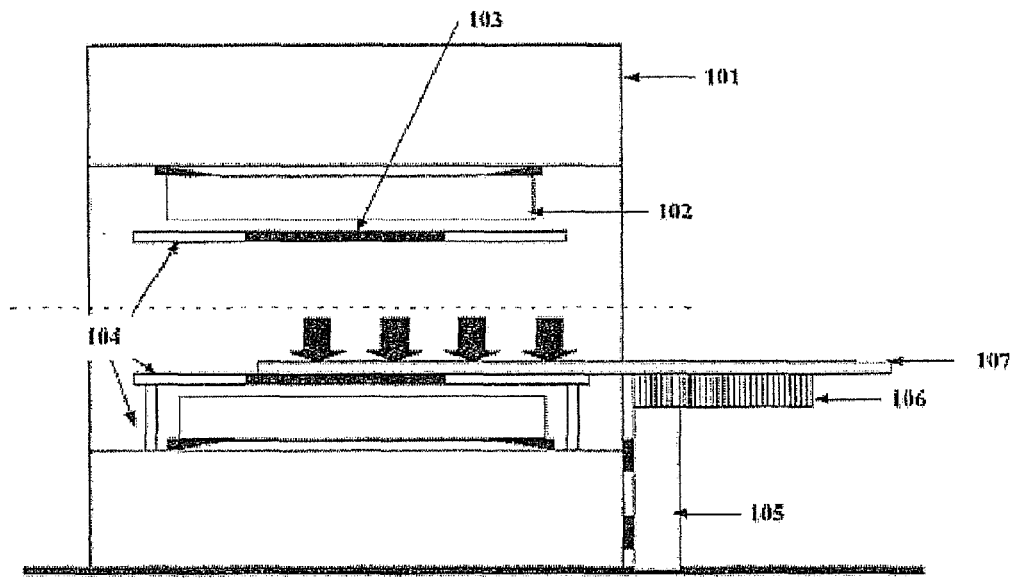
FIG. 1 is a schematic view of a currently available implementation of a patient table used in a magnetic resonance system.
Figure 2:
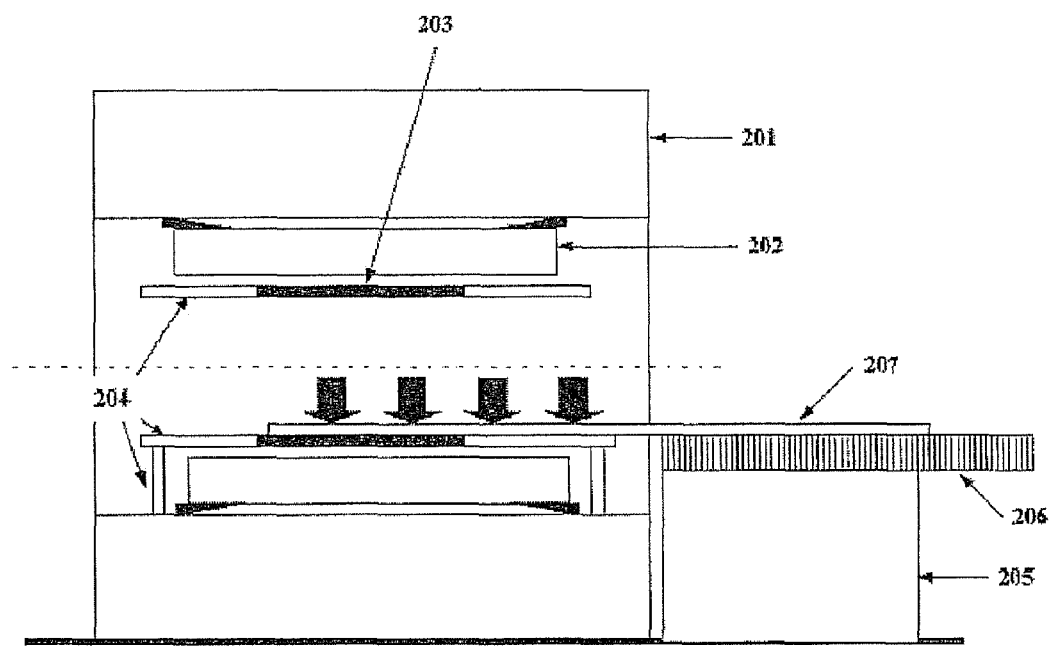
FIG. 2 is a schematic view of another currently available implementation of the patient table used in the magnetic resonance system.
Figure 3:
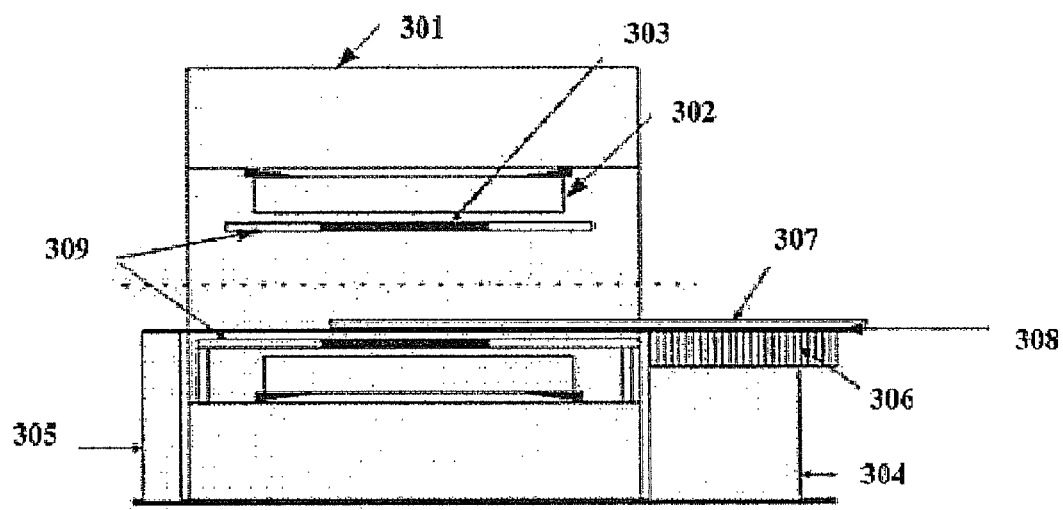
FIG. 3 is a schematic view of the construction structure of a first embodiment of the patient table of the present utility model used in the magnetic resonance system.

In actual applications, the abovementioned patient table can be implemented in various particular forms. The solution of the present utility model will be further described in detail below by way of particular embodiments:

FIG. 3 is a schematic view of the construction structure of a first embodiment of the patient table of the present utility model for use in a magnetic resonance system. As shown in FIG. 3, the magnetic resonance system of this embodiment mainly comprises other currently available construction components such as a magnet 301, a gradient coil 302, a body coil 303, a body coil tube 309, and a patient table (other irrelevant construction components are not shown); wherein, the patient table further comprises: a first supporting frame 304, a second supporting frame 305, a driving mechanism 306, a table board 307 and a travel rail 308. In which case, the first supporting frame 304, the second supporting frame 305, the driving mechanism 306, and the travel rail 308 can be generally referred to as supporting means for the table board 307.

The first supporting frame 304 and the second supporting frame 305 are located respectively at two sides of the magnet 301 without contacting the magnet 301, i.e., it is independent of the gradient coil 302, and the first supporting frame 304 and the second supporting frame 305 can be fixed on the ground, so as to support respectively the two ends of the travel rail 308 of the table board 307; there is a certain gap between the travel rail 308 and the body coil 303 without contact therebetween; and the driving mechanism 306 drives the table board 307 to move on the travel rail 308. As shown in FIG. 3, the driving mechanism 306 can be located between the first supporting frame 304 and the travel rail 308.

By adopting the implementation model shown in FIG. 3, since the table board is supported by two supporting frames independent of the magnet, and it does not contact any object that generates vibration, the vibration of the gradient coil will not be transmitted to the table board, thus it can eliminate completely the mechanical vibration between the gradient coil and the table board, furthermore it avoids the vibration of the scanned object loaded on the table board and improves the imaging quality.

Figure 4:
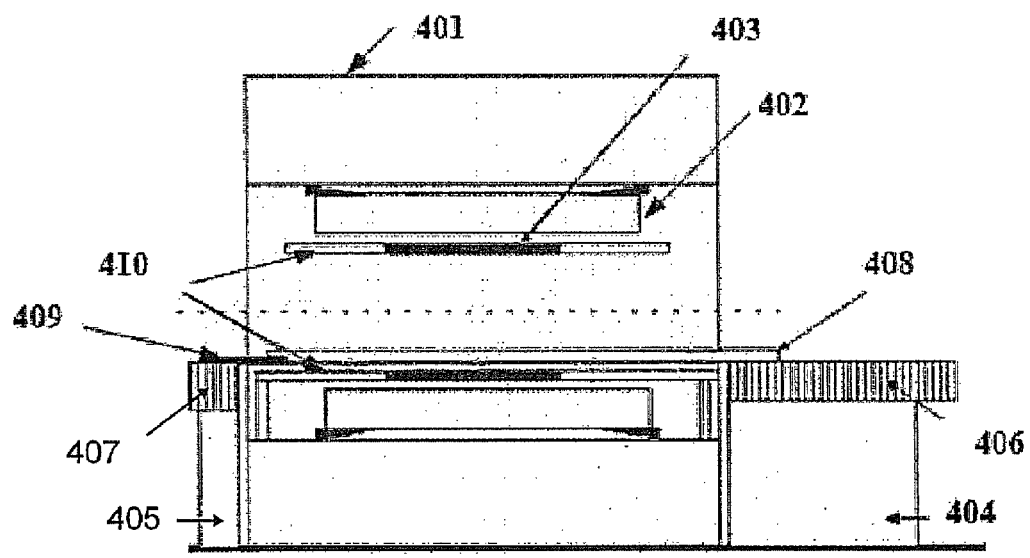
FIG. 4 is a schematic view of the construction structure of a second embodiment of the patient table of the present utility model used in the magnetic resonance system.

FIG. 4 is a schematic view of the construction structure of a second embodiment of the patient table used in the magnetic resonance system described in the present utility model. As shown in FIG. 4, the magnetic resonance system of this embodiment mainly comprises currently available construction components such as a magnet 401, a gradient coil 402, a body coil 403, a body coil tube 410, etc. and a patient table (other irrelevant construction components are not shown); wherein, the patient table further comprises: a first supporting frame 404, a second supporting frame 405, a first driving mechanism 406, a second driving mechanism 407, a supporting member 409 and a table board 408. In which case, the first supporting frame 404, the second supporting frame 405, the first driving mechanism 406, the second driving mechanism 407, and the supporting member 409 can be generally referred to as supporting means for the table board 408. The first supporting frame 404 and the second supporting frame 405 are located respectively at two sides of the magnet 401 without contacting the magnet 401, i.e., being independent of the gradient coil 402; and the first supporting frame 404 and the second supporting frame 405 can be fixed on the ground.

The first driving mechanism 406 drives the table board 408 to move along the rail of the body coil 403 in a horizontal direction, and when the supporting member 409 enters into one end at the bottom of the table board 408, the first driving mechanism drives the first supporting frame 404 to lift the other end of the table board 408 to a predetermined height with a certain gap from the body coil 403;

the supporting member 409 and the second supporting frame 405 are located at the same side, and when the table board 408 is moved along the rail of the body coil 403 to an imaging position, it enters into one end at the bottom of the table board 408 under the driving of the second driving mechanism 407, and is lifted to a predetermined height under the support of the second supporting frame 405; and the second driving mechanism 407, when the table board 408 is moved along the rail of the body coil 403 to the imaging position, drives the supporting member 409 to enter into one end at the bottom of the table board 408, and drives the second supporting frame 405 to lift the supporting member 409 and the table board 408 thereon to a predetermined height with a certain gap from the body coil 403.

As shown in FIG. 4, the first driving mechanism 406 and the second driving mechanism 407 can be located respectively on the first supporting frame 404 and the second supporting frame 405. However, in actual applications, other ways of implementation can also be adopted, for example, the first driving mechanism 406 and the second driving mechanism 407 can be arranged respectively inside corresponding supporting frames, generally speaking, and particular implementation manners are not limited. Furthermore, a person skilled in the art will be able to find out how to implement particularly the functions of the first driving mechanism 406 and the second driving mechanism 407 described in this embodiment according to technical approaches commonly used in the art. Moreover, the manner in this embodiment for the driving mechanism to drive the supporting frame up or down can adopt currently available pneumatic and hydraulic pressure means, and so on. Furthermore, the supporting member 409 in this embodiment can be, as shown in FIG. 4, fixed on the second driving mechanism 407, so that the supporting member 409 can be considered as part of the second driving mechanism 407. When the second supporting frame 405 is lifted, the supporting member 409 is lifted at the same time. The supporting member 409 can be made of materials such as stainless steel and so on, and it needs to be strong enough to support the maximum load of the table board.

The particular operating procedure of the patient table shown in FIG. 4 comprises: when a scan needs to be carried out, the first driving mechanism 406 drives the table board 408 to move along a horizontal direction on the rail of the body coil 403 according to the current manner; when the table board is moved to the imaging position, a small supporting member 409 located at the second driving mechanism 407 moves to the bottom of the table board 408 under the driving of the second driving mechanism 407; subsequently, the first driving mechanism 406 and the second driving mechanism 407 drive respectively the first supporting frame 404 and the second supporting frame 405 to lift it by a height of a few millimeters, which height can be predetermined, but it should ensure that the heights for lifting these two sides are the same, so that the table board 408 is in a floating state during scanning. After the completion of the scan, when the table board 408 is moved out of the magnet, the first driving mechanism 406 also can drive the first supporting frame 404 up or down in the vertical direction, so as to facilitate the next object to be scanned, for example, for a patient to get onto the table board 408 for the next scan.

When the implementation manner shown in FIG. 4 is adopted, since during the scan the table board is in completely floated status, which is dissociated with the body coil, i.e., free of any mechanical contact, the vibration of the gradient coil will not be transmitted to the table board, thus it improves the imaging quality.

In summary, by adopting the technical solutions of the embodiments of the present utility model, it can avoid the influence of the vibration by the gradient coil to the table board, improving imaging quality during the scan, thus achieving a magnetic resonance image of high resolution, for example, the size of pixels being smaller than 0.1 millimeter, which is quite possible in the case of the field intensity being 3T, 4T or 7T, and so on. Moreover, it can avoid the absence of signals caused by the dephasing due to the nature of the tissues' elasticity during vibration.

It should be noted that the above embodiments are merely by way of illustration, and are not intended to limit the technical solution of the present utility model. Any modification, equivalent replacement and improvement within the spirit and principle of the present utility model should all be included in the protective scope of the present utility model.

The invention claimed is:

1. A patient table for use in a magnetic resonance system, comprising:
   a table board that is located in a manner which independently floats and passes through or over a body coil of the magnetic resonance system; and
   a supporting device that supports the table board so that the table board has no contact with the body coil, said supporting device comprising a first supporting frame, a second supporting frame, and a driving mechanism;
   wherein the first supporting frame and the second supporting frame include a respective first end to support the table board and a respective second end fixed on a ground at two sides of a magnet of the magnetic resonance system without the first and second supporting frames having direct or indirect contact with the magnet of the magnetic resonance system, said second end being opposite to the first end; wherein said first supporting frame and the second supporting frame are decoupled from the magnet of the magnetic resonance system such that there is a physical separation space between the first and second supporting frames and the magnet of the magnetic resonance system whereby there is no direct or indirect contact between the first and second supporting frame and the magnet of the magnetic resonance system, and wherein when the table board is in an imaging position, the table board is vibrationally decoupled from the magnet of the magnetic resonance system such that a vibration of the magnet of the magnetic resonance system is not transmitted to the table board.

2. The patient table as claimed in claim 1, wherein the supporting device further comprises a travel rail, and wherein the first and second supporting frames are configured to support the travel rail, and the travel rail is configured to support the table board.

3. The patient table as claimed in claim 1, wherein the first supporting frame and the second supporting frame support two ends of the travel rail respectively.

4. The patient table as claimed in claim 1, wherein the driving mechanism drives the table board to move on the travel rail during scanning.

5. The patient table as claimed in claim 1, wherein the driving mechanism is located between the first supporting frame and the travel rail.

6. The patient table as claimed in claim 1, wherein the first supporting frame and the second supporting frame support the travel rail and the body coil with a certain gap there between.

7. The patient table as claimed in claim 1, wherein the supporting device further comprises a second driving mechanism and a supporting member, and wherein said first supporting frame and said supporting member are configured to support the table board.

8. The patient table as claimed in claim 7, wherein the supporting member and the second supporting frame are located at a same side.

9. The patient table as claimed in claim 7, wherein the driving mechanism drives the table board to move in a horizontal direction to an imaging position and drives the first supporting frame up when the supporting member enters into one end at a bottom of the table board to lift the other end of the table board to a predetermined height and to keep the certain gap with the body coil.

10. The patient table as claimed in claim 9, wherein the second driving mechanism drives the supporting member to enter into the one end at the bottom of the table board when the table board is moved to the imaging position and drives the second supporting frame up to lift the supporting member and the table board to a further predetermined height and to keep the certain gap with the body coil.

11. The patient table as claimed in claim 10, wherein the predetermined height is as same as the further predetermined height.

12. The patient table as claimed in claim 7, wherein the driving mechanism drives the first supporting frame up or down when the table board is moved out of the magnet.

13. The patient table as claimed in claim 7, wherein the driving mechanism is located between the first supporting frame and the table board.

14. The patient table as claimed in claim 7, wherein the second driving mechanism is located between the second supporting frame and the supporting member.

15. The patient table as claimed in claim 7, wherein the supporting member is fixed onto the second driving mechanism.

* * * * *